(12) United States Patent
Priour et al.

(10) Patent No.: US 8,288,553 B2
(45) Date of Patent: Oct. 16, 2012

(54) METHOD FOR PREPARING DISUBSTITUTED PIPERIDINE AND INTERMEDIATES

(76) Inventors: Alain Priour, Paris (FR); Alain Bonnet, Château-Thierry (FR); Gilles Oddon, Genas (FR); Alain Mazurie, Vaujours (FR)

( * ) Notice: Subject to any disclaimer, the term of this patent is extended or adjusted under 35 U.S.C. 154(b) by 220 days.

(21) Appl. No.: 12/677,741

(22) PCT Filed: Sep. 12, 2008

(86) PCT No.: PCT/FR2008/001280
§ 371 (c)(1),
(2), (4) Date: Mar. 11, 2010

(87) PCT Pub. No.: WO2009/090320
PCT Pub. Date: Jul. 23, 2009

(65) Prior Publication Data
US 2010/0197928 A1 Aug. 5, 2010

(30) Foreign Application Priority Data
Sep. 14, 2007 (FR) .................. 07 06449

(51) Int. Cl.
C07D 211/56 (2006.01)
(52) U.S. Cl. ...................................... 546/244
(58) Field of Classification Search .............. None
See application file for complete search history.

(56) References Cited

U.S. PATENT DOCUMENTS

| | | | |
|---|---|---|---|
| 7,112,592 B2 | 9/2006 | Lampilas et al. |
| 7,148,322 B2 | 12/2006 | Boffelli et al. |
| 7,288,549 B2 | 10/2007 | Aszodi et al. |
| 7,396,934 B2 | 7/2008 | El-Ahmad et al. |
| 7,439,253 B2 | 10/2008 | Lampilas et al. |
| 7,612,087 B2 | 11/2009 | Aszodi et al. |
| 7,638,529 B2 | 12/2009 | Lampilas et al. |
| 2007/0105760 A1 | 5/2007 | Boffelli et al. |
| 2007/0299108 A1 | 12/2007 | Aszodi et al. |
| 2009/0018329 A1 | 1/2009 | Lampilas et al. |
| 2009/0215747 A1 | 8/2009 | Aszodi et al. |
| 2010/0048528 A1 | 2/2010 | Aszodi et al. |

FOREIGN PATENT DOCUMENTS

| | | |
|---|---|---|
| WO | WO 02/10172 | 2/2002 |
| WO | WO 02/100860 | 12/2002 |
| WO | WO 03/063864 | 8/2003 |
| WO | WO 2004/052891 | 6/2004 |

OTHER PUBLICATIONS

Baldwin, Jack E. et al.; "A Novel Entry to Carbenoid Species Via β-Ketosulfoxonium Ylides;" J. Chem. Soc. Chem. Commun., 1993; pp. 1434-1435.
Bailey, Patrick D. et al.; "Chiral Synthesis of 5-Hydroxy-(L)-Pipecolic Acids From (L)-Glutamic Acid;" Tetrahedron Letters, vol. 29, No. 18, 1988; pp. 2231-2234.

*Primary Examiner* — Janet Andres
*Assistant Examiner* — Heidi Reese

(57) ABSTRACT

The disclosure relates to a method for preparing a compound of formula (I),

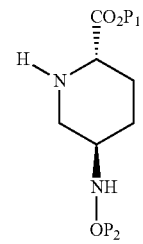

(1)

wherein $P_1$ and $P_2$ are groups protecting the carboxylic acid and oxyamine functions, starting from pyroglutamic acid (S). The disclosure also relates to novel intermediates.

10 Claims, No Drawings

METHOD FOR PREPARING DISUBSTITUTED PIPERIDINE AND INTERMEDIATES

CROSS-REFERENCE TO RELATED APPLICATIONS

This application is a National Phase Entry of International Application No. PCT/FR2008/001280, filed on Sep. 12, 2008, which claims priority to French Application 0706449, filed on Sep. 14, 2007, both of which are incorporated by reference herein.

BACKGROUND AND SUMMARY

The invention relates to a method for preparing a 2,5-disubstituted pyridine and novel intermediates.

PCT Application WO 02/10172 discloses novel azabicyclic compounds useful as drugs in the anti-bacterial field and their preparation using intermediate compounds of formula (A):

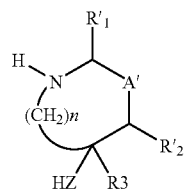

wherein $R'_1$, $R'_2$, $R_3$, Z and n are as defined in said application, and notably among these intermediate compounds, a piperidine of formula ($A_1$):

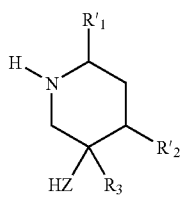

corresponding to a compound of formula (A) wherein n=1 and $A'=CH_2$.

Among the compounds of formula ($A_1$), the compound with the following formula (I) is of particular interest:

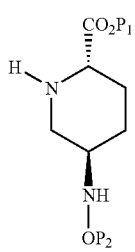

wherein
  $P_1$ and $P_2$ represent protecting groups of carboxylic acid and oxyamine functions, known to those skilled in the art, and notably those mentioned in PCT Application WO 02/10172.

The compound of formula (I) is in the form of a mixture of isomers (2S,5R) and (2S,5S). The compound of formula (I) may be obtained as described in PCT Application WO 02/10172, notably in Example 32, starting from protected cis-5-hydroxy-piperidine-2-carboxylic acid.

The object of the present invention is a novel method for preparing the compound of formula (I), characterized in that the compound of formula (b):

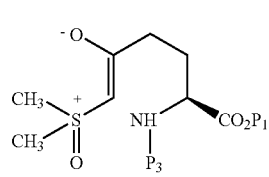

wherein $P_1$ and $P_3$ represent protecting groups of the carboxylic acid function and of the nitrogen,
is treated by a HCl generating reagent, in order to obtain the compound of formula:

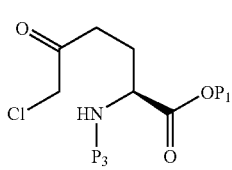

wherein $P_1$ and $P_3$ are defined as here above,
which is treated, without being isolated, with a hydroxylamine derivative, in order to obtain the compound of formula:

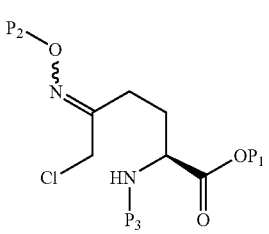

wherein $P_1$ and $P_3$ are defined as here above and $P_2$ represents a protecting group of the oxime, the amine of which is deprotected by the action of an acid, in order to obtain the compound of formula:

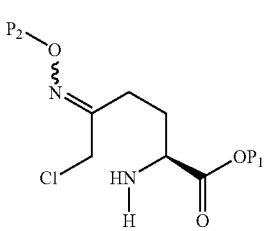

wherein P₁ and P₂ are as defined here above,
which is cyclized by the action of a base in order to obtain the compound of formula:

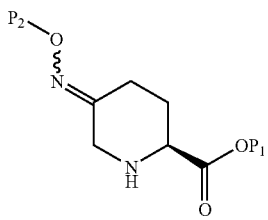

(V)

wherein P₁ and P₂ are defined as here above,
the oxime function of which is reduced by the action of a reducing agent, in order to obtain the expected compound of formula (I) which, if desired, is put in the form of a salt by the action of an acid.

The beta-ketosulfoxonium compound of formula (b) may be obtained starting with the protected (S) pyroglutamic acid of formula (a):

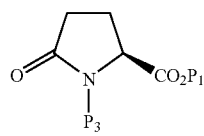

(a)

wherein P₁ and P₃ are defined as here above,
the ring of which is opened by the action of trimethylsulfoxonium iodide in the presence of sodium hydride in tetrahydrofurane.

The protecting group of the carboxylic acid function P₁ is notably an alkyl, allyl, benzyl or p-nitrobenzyl ester residue; equivalent residues known to those skilled in the art may of course also be suitable. P₁ preferably is a benzyl group. The protecting group of the nitrogen P₃ notably forms a carbamate and preferably is a tert-butoxycarbonyl or benzyloxycarbonyl group, it may also be an electro-withdrawing group such as those known to one skilled in the art and referenced in "Greene" (Protective Groups in Organic Synthesis, 3$^{rd}$ edition). P₃ preferably is a tert-butoxycarbonyl group.

The protecting group of the hydroxylamine P₂ is notably a benzyl or allyl residue. P₂ preferably is a benzyl group.

The conditions generating HCl and allowing preparation of the compound of formula (II) preferably consist of using lithium chloride in the presence of a strong acid. Hydrochloric acid may also simply be used. The strong acid is for example hydrochloric acid, sulfuric acid, sulfonic acid such as methane sulfonic acid or ethane sulfonic acid. According to a preferred condition of carrying out the invention, lithium chloride is used in the presence of methane sulfonic acid. This is performed for example within an ether such as tetrahydrofurane or dioxane, within dimethylsulfoxide or within an ester such as ethyl acetate. The protection of the ketone function of the compound of formula (II) is achieved without isolation of the intermediate, depending on the selected protective group, under conditions known to those skilled in the art.

Deprotection of the amine function is achieved by the action of an acid, for example hydrochloric acid, sulfonic acid, trifluoroacetic acid or an alkane sulfonic acid. Depending on the nature of the protective group, these conditions are known to one skilled in the art. Advantageous conditions consist of using a tert-butoxycarbonyl group and of cleaving it by the action of methane sulfonic acid. This may be performed for example in ethyl acetate.

The protected α-chlorooxime of formula (III) is preferably used without being isolated, i.e. in solution in the reaction solvent. The same applies for the protected α-chlorooxime of formula (IV). The base used for cyclizing the compound of formula (IV) is for example an alkaline hydroxide, carbonate or bicarbonate, preferably sodium bicarbonate, or a base of the amine type, for example triethylamine. The reducing agent used for reducing the oxime function is for example a reagent of the alkaline borohydride, diborane or borane-pyridine type in the presence of an acid, for example hydrochloric acid. This may be performed within an alcohol such as methanol or ethanol, or within another organic solvent such as dichloromethane.

The salification of the compound of formula (I) is, if necessary, achieved by adding to the compound an acid in a soluble phase. Among the salts of the acids used for obtaining the products of formula (I), mention may be made, inter alia, to those formed with inorganic acids, such as hydrochloric, hydrobromic, hydroiodic, sulfuric or phosphoric acids, or with organic acids such as formic, acetic, trifluoroacetic, propionic, benzoic, maleic, fumaric, succinic, tartaric, citric, oxalic, glyoxylic, aspartic, alkanesulfonic acids, such as methane and ethane sulfonic acids, arylosulfonic acids such as benzene- and paratoluene-sulfonic acids. The salts are preferably those which allow easy crystallization. The oxalic acid salt is particularly preferred.

Compounds of the type (a) and (b) as well as of the type (II) the formulae of which are indicated above, are known, and mention may be made to the articles of J. Chem. Soc. Chem. Comm. 1993, p. 1434-1435 and Tet. Letters Vol. 29, No. 18, p. 2231-4 (1988). Steps aimed at cyclizing the compounds (B) and (II) were tried.

Cyclization of compound (b) is possible but involves the use of a rhodium-based reagent. Application of this type of reagent on an industrial scale is not a very practical proposition and is very costly. Further, the yields obtained are not satisfactory. Alternatives to rhodium have been sought unsuccessfully.

Cyclization of compound (II) was however unable to be achieved, probably due to the reactivity of the carbonyl group. The present invention provides a method for preparing the intermediate formula (I) under particularly attractive conditions, with an overall yield of the order of 70% and which therefore allows the failure encountered earlier to be overcome. The compounds of formula (III), (IV) and (V) obtained using the method are novel and also constitute a subject matter of the invention, as novel industrial compounds and notably intermediate compounds required for preparing the compounds of formula (I).

DETAILED DESCRIPTION

The following example illustrates the invention.

Example (2S)-5-benzyloxyamino-piperidine-2-carboxylic acid, benzylester and its oxalate Preparation: (5S)-5-tert-butyloxycarbonylamino-6-benzyl-oxy-2,6-ioxohexylidedi-methylsulfoxonium Sodium hydride (60% in oil, 15 g, 0.375 mol) is added to a solution of trimethylsulfoxonium iodide in THF (0.4 l) under stirring at room temperature. The reaction mixture is diluted with DMSO (0.5 l) and is then cooled to −10° C. A solution of L-benzyl-N-Boc-glutamate (100 g, 0.313 mol) in THF (0.35 l) is added. The reaction mixture is warmed up to 0° C., stirred for 45 minutes and then added to a mixture of ammonium chloride (450 g), of water (1.5 l) and ethyl acetate (0.5 l) at 20° C. The organic phase is isolated and washed with a solution of ammonium chloride (180 g) in water (0.6 l) and then with a solution of sodium chloride (200 g) in water (0.6 l). The aqueous phases are extracted with ethyl acetate. The combined organic phases are dried and then the product is precipitated by concentrating the solution under reduced pressure at 20° C. down to a volume of 0.4 l, and by then adding methyl-tert-butyl ether (0.25 l). The suspension is cooled to −10° C., stirred for 2 hours, filtered and then washed with an ethyl-acetate/methyl-tert-butyl ether mixture (7:3, 1×50 ml). The crystals are dried at 40° C. under reduced pressure in order to obtain the expected β-keto-sulfoxonium (114.7 g, 279 mol, 89% yield).

NMR δ (400 MHz, MeOD) 1.49 (s, 9H, $C_4H_9$), 1.92 (m, 1H), 2.13 (m, 1H), 2.26 (m, 2H), 3.50 (s, 6H, $S(CH_3)_2$), 4.20 (m, 1H), 5.25 (m, 2H), 7.45 (m, 5H, $C_6H_5$).

Stage A: (S)-5-(benzyloxyimino)-2-tert-butoxycarbonyl-amino-6-chloro-hexanoic acid benzyl ester (E+Z)

Methanesulfonic acid (29.3 g, 0.305 mol) is slowly added to a mixture of β-keto-sulfoxonium (114 g, 0.277 mol) and of lithium chloride (13.3 g, 0.314 mol) in THF (1.71 ml) at room temperature. The reaction mixture is heated to 50° C. for 5 hours and then cooled at room temperature. Benzylhydroxylamine hydrochloride (46.4 g, 0.291 mol) and sodium acetate (29.6 g, 0.361 mol) are added. The reaction mixture is diluted with ethyl acetate (0.5 l) and water (0.5 l) and then stirred at room temperature for 18 hours. The organic phase is isolated, concentrated down to a volume of 0.4 l and then washed with a sodium chloride solution (25 g) in water (0.25 l). The aqueous phase is separated and then extracted with ethyl acetate (0.2 l). The organic phases are combined and stirred for 1 hour with sodium sulfate (100 g). The mixture is filtered and rinsed with ethyl acetate (2×0.1 l). The α-chlorooxime solution is kept in the refrigerator for the next step where it will be used as such (130.8 g, 0.275 mol, 99.3% yield).

NMR δ (400 MHz, $CDCl_3$) 1.45 (s, 9H, $C_4H_9$), 1.96 (m, 1H, $CH_AH_B$), 2.16 (m, 1H, $CH_AH_B$), 2.47 (m, 2H, $CH_2$), 4.06 and 4.20 (2s, 2H, $CH_2Ph$), 4.38 (m, 1H), 5-5.4 (m, 4H), 7.35 (m, 10H, 2×$C_6H_5$); m/z (+ESI, LCMS) detected 475.0 [$MH^+$].

Stage B: (S)-5-(benzyloxyimino)-piperidine-2-carboxylic acid benzyl ester (E+Z)

The α-chlorooxime solution (0.275 mol) is dried by azeotropic distillation down to a volume of 0.5 l and then diluted with ethyl acetate (0.5 l). The solution is cooled to 0° C. Methane sulfonic acid (136 g, 1.42 mol) is added within 15 minutes. The reaction mixture is heated to 40° C. for 1 hour and then cooled to room temperature before being added to a sodium bicarbonate solution (279 g, 3.40 mol) in water (1 l). The reaction mixture is heated to 50° C. for 3 hours and then cooled to room temperature. The organic phase is isolated and then washed with a sodium chloride solution (50 g) in water (0.5 l)). The aqueous phases are extracted with ethyl acetate (0.5 l). The organic phases are combined. The solution is mixed with silica (100 g) and then for 20 minutes. The solution is filtered and then washed with ethyl acetate. The piperidine-oxime solution is concentrated down to a volume of 0.2 l and then kept in the refrigerator for the next step (88.8 g, 0.262 mol, 95.3% yield).

The E and Z isomers of the oximes are separated by chromatography and then analyzed by NMR;

NMR assumed isomer E δ (400 MHz, $CDCl_3$) 1.8 (m, 1H), 2.25 (m, 3H), 3.15 (m, 1H), 3.35 (d, 1H), 3.62 (d, 1H), 3.64 (d, 1H), 5.1 (s, 2H, $CH_2Ph$), 5.2 (s, 2H, $CH_2Ph$), 7.37 (m, 10H, 2×$C_6H_5$);

NMR assumed isomer Z δ (400 MHz, $CDCl_3$) 1.9 (m, 1H), 2.20-2.60 (m, 4H), 3.35 (d, 1H), 3.64 (d, 1H), 4.3 (d, 1H), 5.1 (s, 2H, $CH_2Ph$), 5.2 (s, 2H, $CH_2Ph$), 7.37 (m, 10H, 2×$C_6H_5$).

Stage C: (2S)-5-(benzyloxyamino)-piperidine-2-carboxylic acid benzyl ester and its oxalate ((2S,5R) and (2S,5S) mixture ~50/50)

The acetate, in which the piperidine-oxime obtained in stage B is in solution, is replaced with methanol by distillation and then diluted down to a volume of 0.2 L. The piperidine-oxime solution (0.261 mol) is added within 30 minutes to an HCl solution (1.32 mol) in methanol (0.31 l) at 0° C. Borane-pyridine (45.4 g, 0.49 mol) is added within 4 hours to the reaction mixture at 0° C. The mixture is warmed up to room temperature and then stirred for one night. The solution is concentrated down to a volume of 0.18 l and then diluted with dichloromethane (0.36 l) and water (0.36 l). An aqueous 50% soda solution is added up to a pH of 7. The aqueous phase is separated and then extracted with dichloromethane (0.27 l). The organic phase is washed with water. The solution of (2S)-5-(benzyloxyamino)-piperidine-2-carboxylic acid benzyl ester is taken up and the dichloromethane is replaced with ethyl acetate by distillation and then dilution to a volume of 0.72 L. An oxalic acid (23.78 g) solution in ethyl acetate (0.27 l) is added within 40 minutes. The suspension is stirred for 2 hours at room temperature, filtered, washed with ethyl acetate (3×90 ml) and dried at 30° C. in order to obtain oxyamine oxalate as a powder (95.32 g, 0.221 mol, 85% yield).

The invention claimed is:
1. A method for preparing the compound of formula (I)

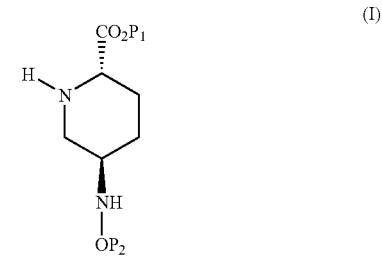

(I)

wherein $P_1$ and $P_2$ represent groups protecting the carboxylic acid and oxyamine functions, comprising a beta-ketosulfoxonium compound of formula:

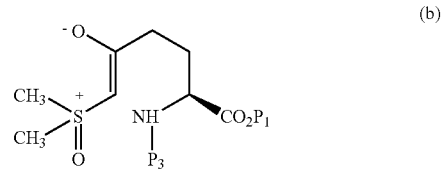

(b)

wherein $P_1$ is as defined here above and $P_3$ represents an amine protecting group, is treated with a reagent generating HCl, in order to obtain the compound of formula:

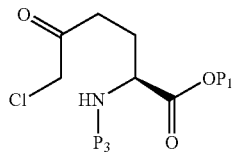
(II)

wherein $P_1$ and $P_2$ are as defined here above, which is treated without isolating it, with hydroxylamine derivative, in order to obtain the compound of formula:

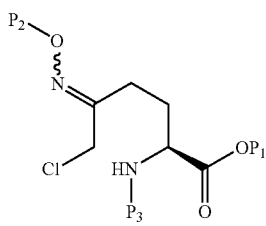
(III)

wherein $P_1$ and $P_3$ are as defined here above and $P_2$ represents a protecting group of the oxime, the amine of which is de-protected by the action of an acid, in order to obtain the compound of formula:

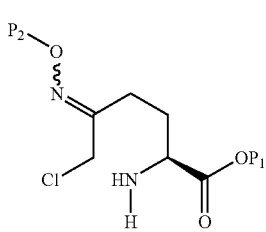
(IV)

wherein $P_1$ and $P_2$ are defined as here above, which is cyclized by the action of a base, in order to obtain the compound of formula:

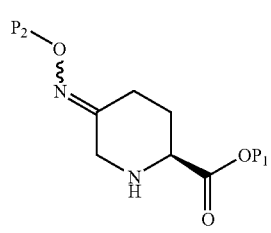
(V)

wherein $P_1$ and $P_2$ are defined as here above, the oxime function of which is reduced by the action of a reducing agent, in order to obtain the expected compound of formula (I) which, if desired, is salified by the action of an acid.

2. The method according to claim 1, wherein $P_1$ represents a benzyl group.

3. The method according to claim 1, wherein $P_3$ represents a tert-butoxy-carbonyl group.

4. The method according to claim 1, wherein $P_2$ represents a benzyl group.

5. The method according to claim 1, wherein the compound of formula (b) is treated with lithium chloride in the presence of methane sulfonic acid.

6. The method according to claim 1, wherein the amine of the compound of formula (III) is de-protected by the action of methane sulfonic acid, without prior isolation of this compound.

7. The method according to claim 1, wherein the cyclization of the compound of formula (IV) is carried out by the action of sodium bicarbonate.

8. A compound of formula

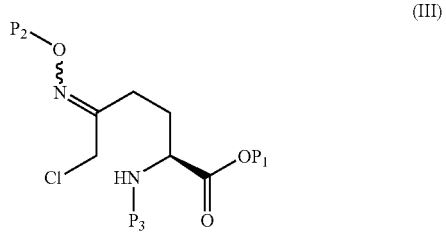
(III)

wherein $P_1$ represents a group protecting the carboxylic acid function, $P_2$ represents a group protecting the oxyamine function and $P_3$ represents an amine protecting group.

9. A compound of formula (IV):

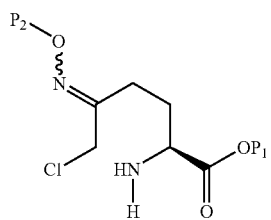
(IV)

wherein $P_1$ represents a group protecting the carboxylic acid function and $P_2$ represents a group protecting the oxyamine function.

10. A compound of formula (V):

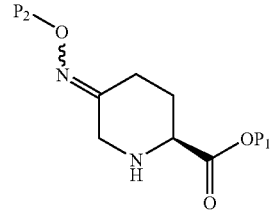
(V)

wherein $P_1$ represents a group protecting the carboxylic acid function and $P_2$ represents a group protecting the oxyamine function.

* * * * *